US012053606B2

(12) United States Patent
Pless et al.

(10) Patent No.: US 12,053,606 B2
(45) Date of Patent: Aug. 6, 2024

(54) OPIOID OVERDOSE RESCUE DEVICE

(71) Applicant: Celero Systems, Inc., Lincoln, MA (US)

(72) Inventors: Benjamin D. Pless, Lincoln, MA (US); Daniel Bacher, Walpole, MA (US)

(73) Assignee: CELERO SYSTEMS, INC., Lincoln, MA (US)

( * ) Notice: Subject to any disclaimer, the term of this patent is extended or adjusted under 35 U.S.C. 154(b) by 673 days.

(21) Appl. No.: 17/007,086

(22) Filed: Aug. 31, 2020

(65) Prior Publication Data

US 2021/0060317 A1 Mar. 4, 2021

Related U.S. Application Data

(60) Provisional application No. 63/044,523, filed on Jun. 26, 2020, provisional application No. 63/029,745, (Continued)

(51) Int. Cl.
| | |
|---|---|
| *A61M 31/00* | (2006.01) |
| *A61K 9/00* | (2006.01) |
| *A61K 9/48* | (2006.01) |
| *A61K 31/485* | (2006.01) |
| *A61P 25/36* | (2006.01) |

(52) U.S. Cl.
CPC ........... *A61M 31/00* (2013.01); *A61K 9/0065* (2013.01); *A61K 9/4808* (2013.01); *A61K 31/485* (2013.01); *A61P 25/36* (2018.01); *A61M 2205/18* (2013.01); *A61M 2205/3303* (2013.01); *A61M 2205/3306* (2013.01); *A61M 2205/3523* (2013.01); *A61M 2205/3553* (2013.01); *A61M 2205/50* (2013.01); *A61M 2205/52* (2013.01); *A61M 2210/1042* (2013.01); *A61M 2230/04* (2013.01); *A61M 2230/06* (2013.01);
(Continued)

(58) Field of Classification Search
CPC . A61M 31/002; A61M 5/1723; A61K 9/0053; A61K 9/0097
See application file for complete search history.

(56) References Cited

U.S. PATENT DOCUMENTS

| | | |
|---|---|---|
| 10,086,138 B1 | 10/2018 | Novak, Jr. |
| 10,625,063 B2 | 4/2020 | Altschul et al. |

(Continued)

FOREIGN PATENT DOCUMENTS

WO 2019/023473 A1 1/2019

*Primary Examiner* — Emily L Schmidt
(74) *Attorney, Agent, or Firm* — Tarolli, Sundheim, Covell & Tummino LLP

(57) ABSTRACT

An opioid overdose rescue device is provided that includes an ingestible capsule. Within the ingestible capsule is a non-refillable drug dispenser comprising an opioid antidote and at least one sensor configured to detect at least one physiological parameter indicative of an opioid overdose. A controller is also contained within the ingestible capsule and is operatively coupled to the drug dispenser and the least one sensor. The controller is configured to receive a signal detected by the least one sensor of the at least one physiological parameter to actuate release of the opioid antidote from the drug dispenser into the intestine of the patient upon a determination that the at least one physiological parameter falls outside a threshold value or range for the at least one physiological parameter indicating that an opioid overdose has been detected.

18 Claims, 8 Drawing Sheets

Related U.S. Application Data filed on May 26, 2020, provisional application No. 62/966,105, filed on Jan. 27, 2020, provisional application No. 62/949,835, filed on Dec. 18, 2019, provisional application No. 62/937,325, filed on Nov. 19, 2019, provisional application No. 62/911,723, filed on Oct. 7, 2019, provisional application No. 62/894,724, filed on Aug. 31, 2019.

(52) U.S. Cl.
CPC ..... *A61M 2230/20* (2013.01); *A61M 2230/30* (2013.01); *A61M 2230/42* (2013.01); *A61M 2230/50* (2013.01); *A61M 2230/63* (2013.01); *A61M 2230/65* (2013.01)

(56) References Cited

U.S. PATENT DOCUMENTS

| | | | |
|---|---|---|---|
| 10,661,010 B1 | 5/2020 | Tsinberg | |
| 2009/0030481 A1* | 1/2009 | Lindenthaler | A61N 1/36007 607/48 |
| 2012/0209086 A1* | 8/2012 | Beute | A61B 5/7285 600/479 |
| 2015/0238138 A1* | 8/2015 | Lehmann | A61B 5/743 600/301 |
| 2017/0127993 A1* | 5/2017 | Olivier | A61B 5/02055 |
| 2017/0181641 A1* | 6/2017 | Olivier | A61B 5/7278 |
| 2018/0147343 A1 | 5/2018 | Tyson | |
| 2018/0228969 A1 | 8/2018 | MacDonald | |
| 2018/0264242 A1 | 9/2018 | Hoffman et al. | |
| 2018/0296123 A1* | 10/2018 | Karakaya | G16H 40/63 |
| 2019/0046038 A1* | 2/2019 | Weinstein | A61B 5/0024 |
| 2019/0060568 A1* | 2/2019 | Newberry | A61B 5/14551 |
| 2019/0125256 A1 | 5/2019 | Hays | |
| 2019/0231707 A1* | 8/2019 | Stiles | A61K 47/55 |
| 2019/0374139 A1 | 12/2019 | Kiani et al. | |
| 2020/0023112 A1* | 1/2020 | Hansen | A61M 60/538 |
| 2020/0054568 A1* | 2/2020 | Gross | A61K 9/0053 |
| 2020/0060546 A1* | 2/2020 | Madnani | A61B 5/6838 |
| 2021/0353168 A1* | 11/2021 | Olivier | A61B 5/6802 |

\* cited by examiner

OPIOID OVERDOSE RESCUE DEVICE

CROSS-REFERENCE TO RELATED APPLICATIONS

The present application claims priority to U.S. Provisional Application No. 62/894,724, filed on Aug. 31, 2019; U.S. Provisional Application No. 62/911,723 filed on Oct. 7, 2019; U.S. Provisional Application No. 62/937,325, filed on Nov. 19, 2019; U.S. Provisional Application No. 62/949,835 filed on Dec. 18, 2019; U.S. Provisional Application No. 62/966,105, filed on Jan. 27, 2020; U.S. Provisional Application No. 63/029,745, filed on May 26, 2020 and U.S. Provisional Application No. 63/044,523, filed on Jun. 26, 2020. All the above-referenced application are incorporated herein by reference in their entirety.

TECHNICAL FIELD

The present application relates to an opioid overdose rescue device to mitigate the adverse consequences of an opioid overdose.

BACKGROUND

The opioid epidemic in the United States results in tens of thousands of deaths per year. Fatalities occur when an overdose of an opioid results in depressed respiration and ultimately cardiac failure. Naloxone is an opioid receptor antagonist used to counter the effects of an opioid overdose. Specifically, it is used to counteract life-threatening depression of the central nervous system and respiratory system, allowing an overdose victim to breathe normally. Naloxone can be given by intranasal spray, or by direct injection intramuscularly, subcutaneously, or intravenously. It is a temporary drug that wears off in 20-90 minutes. Due to first pass metabolism in the liver, the oral bioavailability of naloxone is only approximately 2% making it impractical for delivery to the intestine.

U.S. Patent Application Publication No. 2019/0125256 describes a wearable device, such as a nasal cannula, for detecting an overdose and automatically administering a drug. The device includes a sensor configured to measure a condition of a user indicative of an overdose, a container that retains the drug, and a drug delivery device fluidly connected to the sensor and the container. Because the device is wearable it can be cumbersome for the user and can raise compliance issues.

U.S. Pat. No. 10,086,138 describes a drug delivery system that utilizes physiological monitor outputs so as to automatically give a bolus of a drug via an intravenous line when certain criteria and confidence levels are met. An emergency button is provided to manually trigger administration of the drug. Such a system is utilized in a clinical or hospital setting and is not suitable in a home setting, where most accidental opioid overdoses occur.

U.S. Pat. No. 10,661,010 describes an implantable medical device configured to detect opioid overdose symptoms and automatically release opioid overdose medication into the body of a user. The device may be an embedded module inserted in the user's arm and can include a medicine release unit that is replenished externally via a syringe. Since such a device requires a surgical procedure to implant the device, it is invasive by nature and also requires the medical release unit to be re-filled externally which can be time consuming and cumbersome.

As such, there is a need for a device that is user-compliant, non-invasive and that can be administered in a home or non-clinical setting for mitigating the effects of an opioid overdose.

SUMMARY

One embodiment of the present disclosure is directed to the detection of an opioid overdose event. Opioid overdoses are a public health problem of epidemic proportions that are associated with a high likelihood of death. By providing a simple, unobtrusive and convenient platform with which to monitor patients at risk, devices and systems as described herein makes it possible for an overdose to be automatically detected, thereby leading to alarms and lifesaving treatment. By monitoring respiration, heart rate, core temperature, tissue color and SaO2, for example, the device can detect the presence of physiologic distress when individual parameters, trends in parameters or combinations of parameters meet predefined conditions. For example, a trend towards abnormal breathing (e.g. shallow, high rate), declining SaO2 could trigger the ingested device to send an emergency message to a smart phone carried by the patient. The smart phone could then send an emergency message to caregivers or clinicians signaling the need for urgent intervention. If physiological symptoms continue to decline including, for example, change in body temperature, cyanosis of intestinal tissue (i.e. tissue color change from pink to blue) or evidence of tachycardia or bradycardia, the ingested device could also release an opiate receptor antagonist, such as naloxone or nalmefene, according to a prescribed schedule.

In an aspect, an opioid overdose rescue device to mitigate the effects of an opioid overdose in a patient who has taken an opioid is provided. Such a device includes an ingestible capsule and a substrate contained within the capsule. The device can further include an optional anchor connected to the substrate and sized and configured to attach to the mucosal surface of the patient's intestine. The device can further include a non-refillable drug dispenser contained within capsule and can comprise an opioid antidote. At least one sensor can be contained with the capsule and configured to detect at least one physiological parameter that has a threshold value or range indicative of an opioid overdose. A controller can be mounted on the substrate and can be operatively coupled to the drug dispenser and the least one sensor. The controller can be configured to receive a signal detected by the least one sensor of the at least one physiological parameter to actuate release of the opioid antidote from the drug dispenser into the intestine of the patient upon a determination that the at least one physiological parameter falls outside of the threshold value or range for the at least one physiological parameter indicating that an opioid overdose has been detected. The device can further include a power controller electrically connected to the controller.

In another aspect, an opioid overdose rescue device to mitigate the effects of an opioid overdose in a patient who has taken an opioid is provided. The device can include an ingestible capsule and a substrate contained within the capsule. An optional anchor can be connected to the substrate and sized and configured to attach to the mucosal surface of the patient's intestine. The device can further include a non-refillable drug dispenser contained within the capsule and can comprise an opioid antidote. An accelerometer can be contained within the capsule and can be configured to sense motion within the intestine. A controller can be mounted on the substrate and operatively coupled to the drug dispenser and the accelerometer. The controller can be configured to receive motion sensing data from the accelerometer and estimate a respiratory rate of the patient based on the motion sensing data and to actuate drug release of the opioid antidote from the drug dispenser into the intestine of the patient upon a determination that the respiratory rate falls outside a threshold value or range indicating that an opioid overdose has been detected. The device can also include a power controller electrically connected to the controller.

In another aspect, an opioid overdose rescue device to mitigate the effects of an opioid overdose in a patient who has taken an opioid is provided. The device can include an ingestible capsule and a substrate contained within the capsule. An optional anchor can be connected to the substrate and sized and configured to attach to the mucosal surface of the patient's intestine. A non-refillable drug dispenser can be contained within the capsule and can comprise an opioid antidote. A PPG sensor can be contained within the capsule and can be configured to sense PPG data. A controller can be mounted on the substrate and operatively coupled to the drug dispenser and the PPG sensor. The controller can be configured to receive PPG sensing data from the PPG sensor and estimate a respiratory rate of the patient based on the PPG sensing data and to actuate drug release of the opioid antidote from the drug dispenser into the intestine of the patient upon a determination that the respiratory rate falls outside a threshold value or range indicating that an opioid overdose has been detected. The device can also include a power controller electrically connected to the controller.

DETAILED DESCRIPTION

As used herein with respect to a described element, the terms "a," "an," and "the" include at least one or more of the described elements including combinations thereof unless otherwise indicated. Further, the terms "or" and "and" refer to "and/or" and combinations thereof unless otherwise indicated. By "substantially" is meant that the shape or configuration of the described element need not have the mathematically exact described shape or configuration of the described element but can have a shape or configuration that is recognizable by one skilled in the art as generally or approximately having the described shape or configuration of the described element. A "patient" as described herein includes a mammal, such as a human being. An "ingestible capsule" as used herein is a capsule that is not just capable of being ingested but rather is suitable for swallowing and entering into the gastrointestinal tract. By "mitigating the effects of an opioid overdose in a patient" means mitigating the adverse consequences of an opioid overdose in a patient that has taken an opioid prior to taking the ingestible capsule and whose condition improves compared to the patient's condition prior to the overdose.

An opioid overdose rescue device is provided that contains an electronic circuit folded into a small capsule suitable for swallowing. Upon being ingested, the capsule can pass through the patient's stomach and dissolve in the intestine thereby releasing the electronic circuit. Once released, the electronic circuit can attach to the mucosal layer of the intestine where it can reside for a temporary period of time, such as up to one week, for example. Sensors within the capsule can monitor one or more physiological parameters indicative of an opioid overdose such as electrical cardiac activity, heart rate, heart rate variability, respiratory monitoring (e.g. respiratory rate), saturated oxygen, intestinal tissue color, central temperature, bodily motions as detected from the intestine, or combinations thereof. Physiological parameters can be measured by an electrocardiogram (ECG) sensor, an accelerometer, a photoplethysograph (PPG) sensor, a temperature sensor, or combinations thereof. Upon detecting physiological indications of an opioid overdose, the ingested device can release a rescue medication via a drug dispenser as well as send out alerts to the patient and/or a caregiver. Non limiting examples of suitable drug dispensers include MEMS drug delivery, valve systems, osmotic plug pistons, electrolytical pumps, or combinations thereof.

Figure 1:
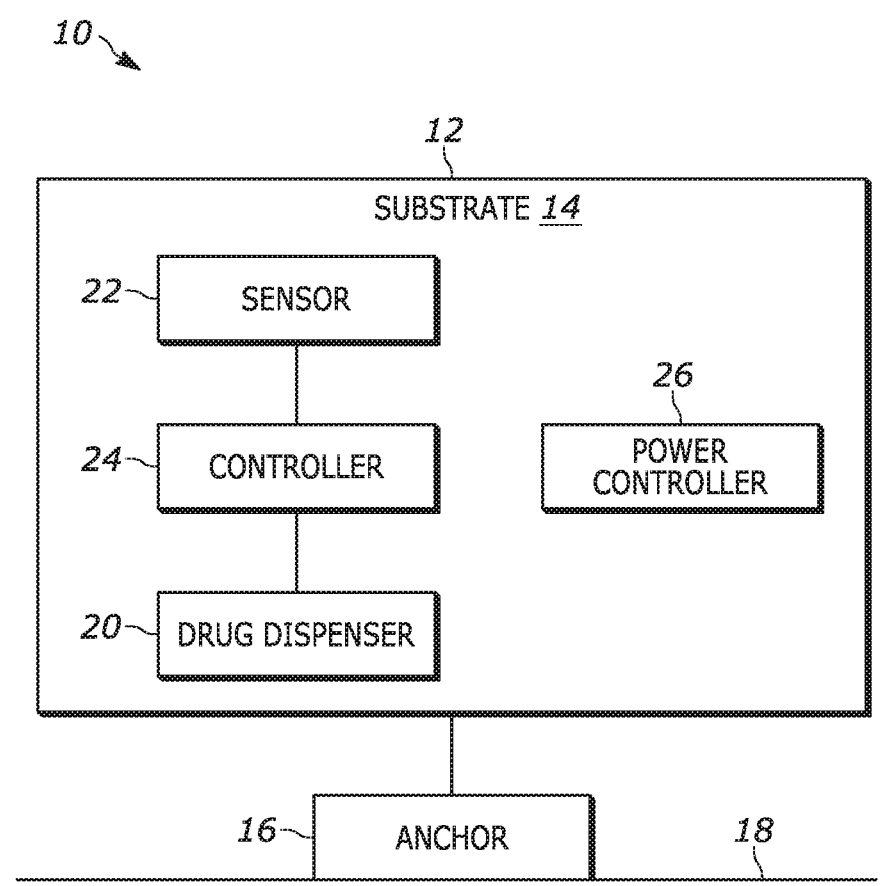
FIG. 1 is a block diagram of an exemplary opioid overdose rescue device according to an aspect of the present disclosure.

Referring to FIG. 1, in an embodiment, an opioid overdose rescue device 10 is provided that includes an ingestible capsule 12, and a substrate 14 contained within capsule 12. An optional anchor 16 can be connected to substrate 14 and sized and configured to attach to the mucosal surface 18 of the patient's intestine. Device 10 can also include a non-refillable drug dispenser 20 contained within capsule 12 and that contains an opioid antidote. The non-refillable drug dispenser is a reservoir that does not include any ports or similar structures that allow the drug dispenser to be re-filled from a location external to the patient's body, such as a syringe containing an opioid antidote that is injected into the drug dispenser from outside the patient's body. Device 10 can also include at least one sensor 22 contained within capsule 12 that is configured to detect at least one physiological parameter indicative of an opioid overdose. Device 10 can also comprise controller 24 mounted on substrate 14 and operatively coupled to drug dispenser 20 and sensor 22. Controller 24 can be configured to receive a signal detected by sensor 22 of the physiological parameter to actuate release of the opioid antidote from drug dispenser 20 into the patient's intestine upon a determination that the physiological parameter falls outside a threshold value or range indicating that an opioid overdose has been detected. Device 10 can also include a power controller 26 electrically connected to controller 24.

Figure 2A:
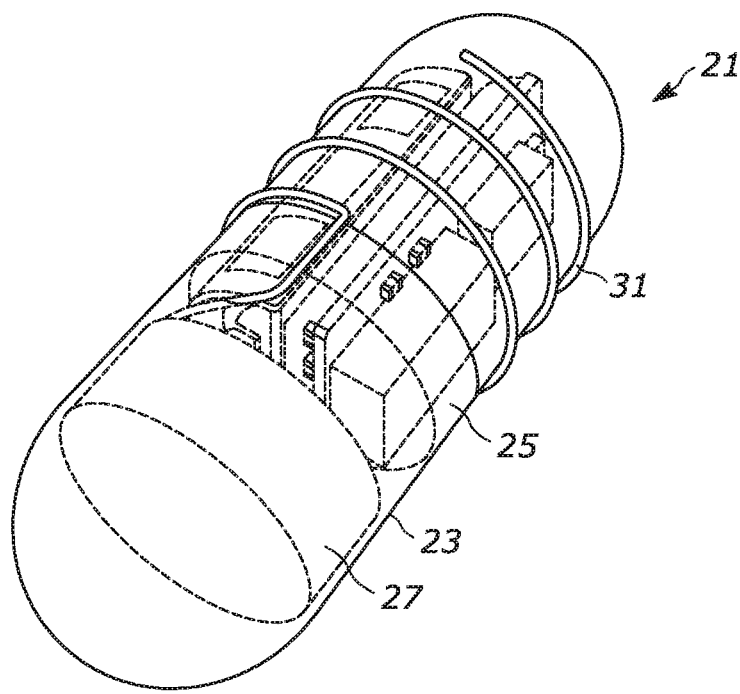
FIG. 2A is a perspective view of an exemplary opioid overdose rescue device according to an aspect of the present disclosure and FIG. 2B is an inverted view of FIG. 2A.
Figure 2B:
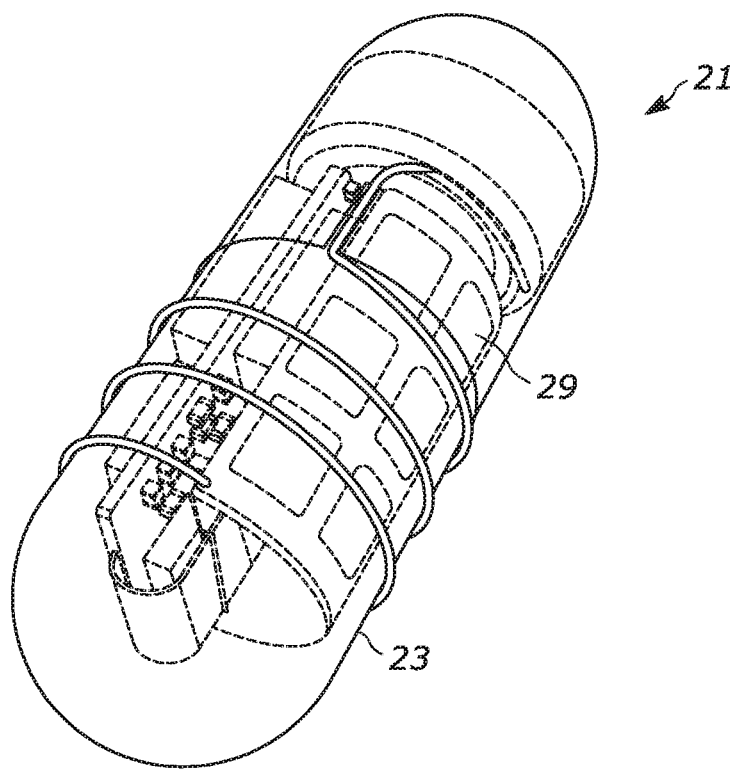

FIGS. 2A and 2B illustrate an exemplary arrangement of certain components of an opioid overdose rescue device 21. For example, device 21 comprises a capsule 23 within which is contained a controller 25, a power controller in the form of a battery 27, and a drug dispenser 29. Disposed about the outer surface of capsule 23 is an antenna 31. The device can comprise other components as described below.

Figure 3:
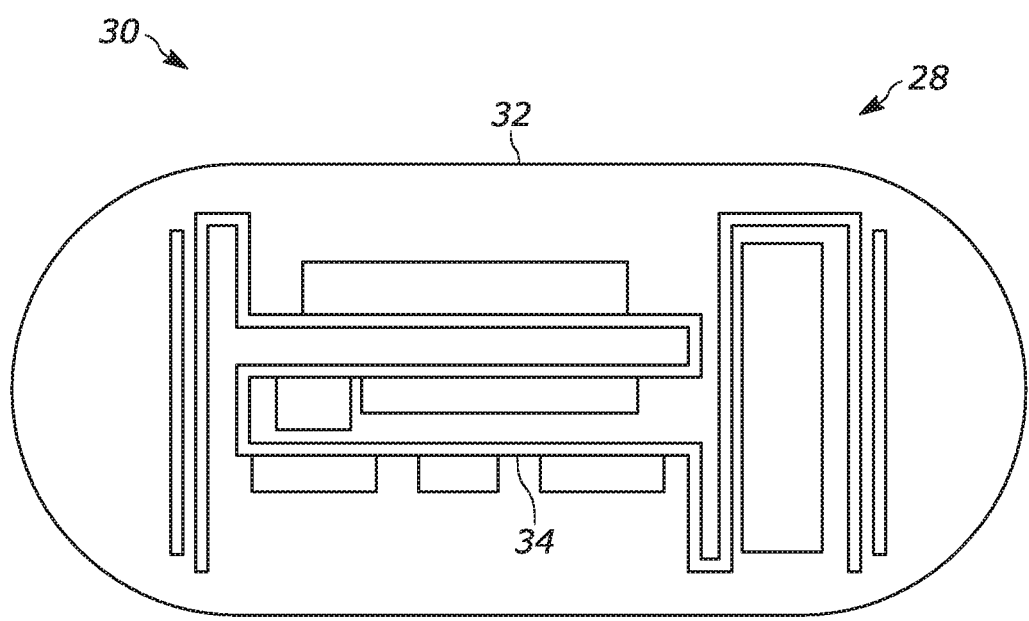
FIG. 3 is a schematic cross-sectional view of an exemplary opioid overdose rescue device where the substrate is in a furled configuration according to an aspect of the present disclosure.

With reference to FIG. 3, an ingestible capsule 28 of an opioid overdose rescue device 30 can be a gelatin capsule or can have another type of suitable enteric coating 32 that allows it to pass through the acidic environment of the stomach and then dissolve upon reaching the neutral pH environment of the intestine. Capsule 28 can have any suitable size for swallowing such as between size 000 to size 4. Substrate 34 can assume a folded compact shape in capsule 28. As such, substrate 34 can be fabricated from a flexible biodegradable material such as, for example, silk, cellulose, or another biodegradable material. Conductors (not shown) in substrate 20 can also be fabricated from a biodegradable material, such as, for example, magnesium alloy. Alternatively, the substrate and/or the conductors can be fabricated from a non-biodegradable material. Mechanical links can be integrally formed on the substrate, separating groups of electrical components. The mechanical links can be fabricated of a biodegradable material. Alternatively, the mechanical links can include a biogalvanic material, such that when energized, the mechanical links rapidly corrode.

Figure 4:
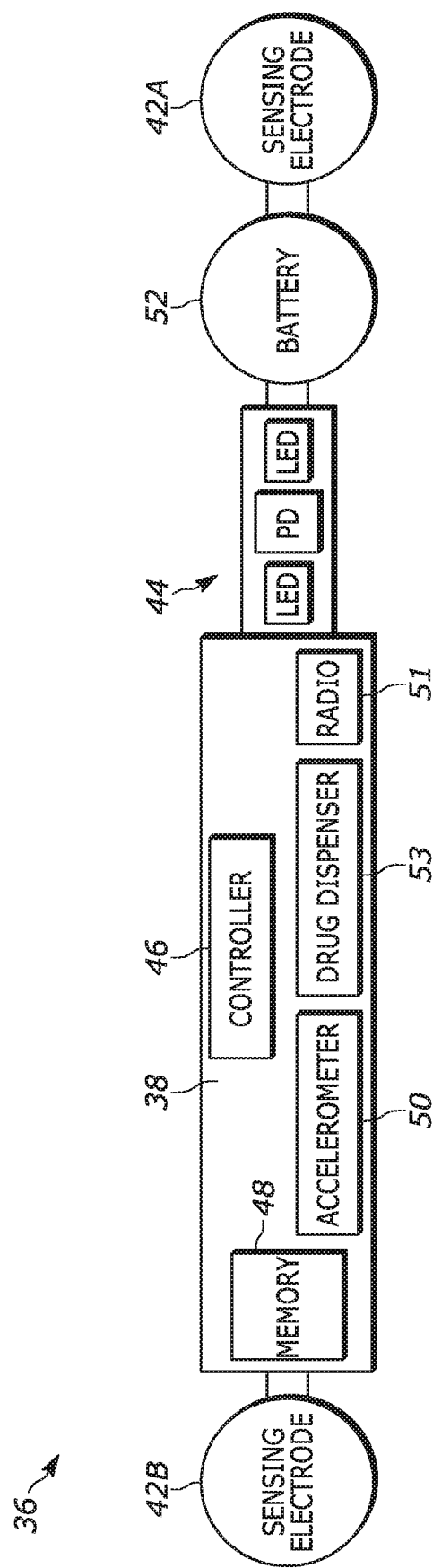
FIG. 4 is a top plan view of an exemplary opioid overdose rescue device where the substrate is in an unfurled configuration according to an aspect of the present disclosure.

FIG. 4 is a top plan view of an exemplary opioid overdose rescue device 36 when substrate 38 is in an unfurled configuration. In this particular aspect, the opioid rescue device comprises a PPG sensor 44, an accelerometer 50, and sensing electrodes 42A and 42B that can be used for ECG monitoring and/or for impedance plethysmography (IPG). However, additional or fewer sensors could be used so long as at least one physiological parameter indicative of an opioid overdose is measured. Device 36 can also include a controller 46, memory 48, a battery 52, a drug dispenser 53, a non-specific radio module, or other wireless communication module 51. The controller, the PPG sensor, and the accelerometer can be formed at least partially as an application specific integrated circuit (ASIC).

Figure 5:
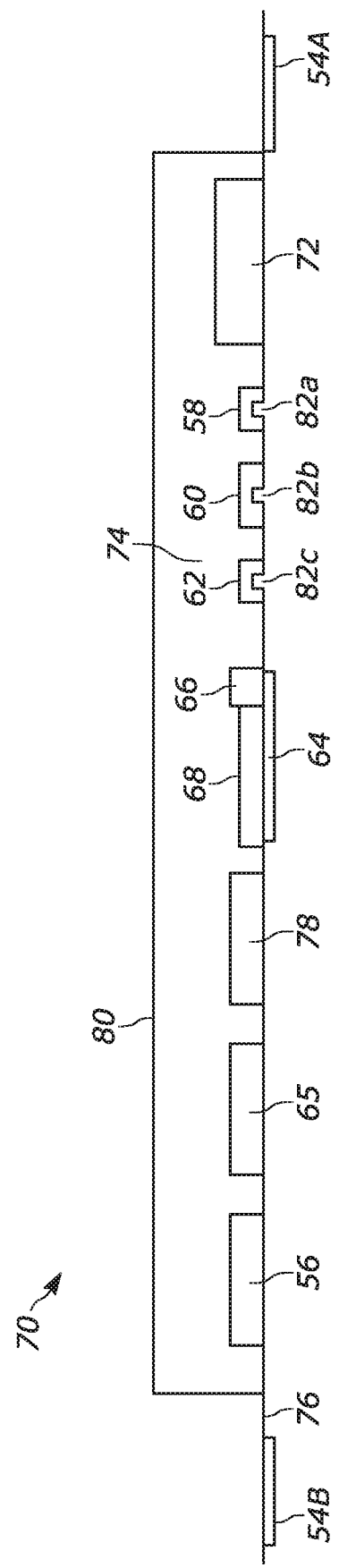
FIG. 5 is side view of an exemplary opioid overdose rescue device according to an aspect of the present disclosure.

Referring to FIG. 5, in this aspect, an opioid overdose rescue device 70 can include ECG/plethysmography electrodes 54A and 54B. Such electrodes can be disposed on a bottom side 76 at either end of substrate 74. A circuit ground electrode 64 can be disposed towards the middle of bottom side 76 of substrate 74. Other components including memory 56, controller 68, communication module 78, a battery bypass capacitor 66, and PPG LEDs 62 and 58 and photodiode 60 can be located on top side 80 of substrate 74. Drug dispenser 65 can be located on either top or bottom surface so long as drug can be released from the dispenser and absorbed into the intestines (e.g. delivered into the lumen or delivered into the intestinal wall). A battery 72 can power device 70. While the pulse PPG components 58, 60, and 62 are illustrated as being on top side 80 they can be directed through apertures 82 towards bottom side 76 which is where the mucosa of the intestine will be.

Top side 80 of the substrate 74 can be coated with a thin hydrophobic coating such as a 5 micron thick layer of parylene. Bottom side 76 of substrate 74 can be coated completely or in part (for example just at one end) with a mucoadhesive such as a hydrogel that contains or is largely formulated from a muco-adhesive such as poly(butadiene-maleic anhydride-co-L-DOPA) (PBMAD) or Carbopol, and other suitable mucoadhesives. When the substrate unfurls the mucoadhesive layer can cause the bottom side 76 of the substrate to lightly adhere to the mucosa on the wall of the intestine. Alternatively, no mucoadhesive or anchor can be disposed on the substrate. Top side 80 of substrate 74 can be disposed towards the lumen of the intestine. Individual circuits (the battery; the memory; the controller and the Bluetooth module as a group); (the LEDs and the photodiode as a group) can each be encapsulated in a thin and conformal coat of a material like silicone or epoxy. This can make the substrate biocompatible and smooth so that chyme and other contents of the intestine can flow with minimal resistance over the top of the substrate. The electrodes are preferably made from a thin film gold about 20 microns thick, but other materials such as conductive polymers or other materials such as silver, platinum, titanium, titanium nitride or iridium oxide may be used. Once ingested and unfolded in the intestinal tract (in this aspect) the device can monitor ECG, respiration, saturated oxygen, tissue color and core temperature (in aspects including a temperature sensor). Most of the functionality can be contained in a custom integrated circuit.

Electrodes can connect to an ECG amplifier and filter, and to a plethysmogram circuit. A ground electrode can provide a reference voltage to the patient and can be connected to a power controller that distributes power from a battery to the rest of the circuits. The power controller can also control the connectivity of a battery bypass capacitor to reduce power consumption before the circuit is activated. The ECG amplifier can provide a gain of about 200 and can be band pass filtered between about 2 Hz and 100 Hz. The plethysmogram can inject a series of (for example) 50 uA current pulses approximately 30 μsec in duration at a rate of about 30 Hz into the electrodes. A synchronous demodulator can construct an envelope of the impedance waveform from the voltage resulting from the current pulses. From the impedance signal, a respiration signal can be derived. The controller can route the output of the plethysmogram or the ECG amplifier to an A to D converter (ADC) for subsequent storage in a memory, such as static RAM (SRAM), for example.

The device can have a crystal controlled real-time clock which can be used for a number of functions including time stamping events and logs stored in the memory. In addition, using the plethysmogram circuit, the device can monitor the impedance across the electrodes and automatically detect when the device has unfurled. The date and time when the device unfurls can be stored as the activation time for the device. At a fixed time later (for example at two weeks), the service life of the device can be programmed to come to an end. As mentioned above, the device can automatically initiate a process to cause mechanical links between circuit elements to break down. This can be done, for example, by energizing biogalvanically corrodible links between the circuit elements. In an alternative embodiment, the biodegradable links can be engineered to be biostable for a period of time (e.g. 10 to 14 days) and then rapidly biodegrade.

In addition to storing the activation time in memory, other event logs may be stored. For example, the controller can analyze the ECG and store the time and date of cardiac events such as tachycardia and bradyarrhythmias. The controller can also analyze the plethysmogram and store the date and time of respiratory events such as apnea, or disordered breathing. In addition, a PPG circuit can work in conjunction with infrared and red LEDS and a photodiode to monitor saturated oxygen (SaO2). The controller can detect changes in SA02, in particular drops of 3% or greater, and store the date and time of these events in the memory. In addition, the PPG signal can be analyzed by the controller to derive a respiration signal. The PPG signals can also be analyzed by the controller to derive relative change in intestinal wall color. An integrated temperature circuit can be sampled by the controller on a regular basis for storage in the memory. In addition to the physiological sensors mentioned above, additional sensors may be used, such as, for example, a microphone, or a pressure sensor.

A Bluetooth radio can communicate directly with a smart phone or other Bluetooth enabled device outside the patient's body. The Bluetooth radio can be a 2.4 GHz Bluetooth or a BLE (Bluetooth Low Energy) radio. The communication link can allow a physician to configure the ingested device to collect certain data and to retrieve the data after it has been collected. In an alternative configuration, wireless data telemetry can be achieved using a sub-GHz frequency radio (specifically 400-900 MHz, including 433 MHz radios) communicating to a small receiver, such as a key fob-sized receiver that could be worn by the patient or otherwise placed on the patient's person that mediates data transfer between the ingested device and a smartphone via Bluetooth.

As stated above, at least one sensor contained with the capsule is configured to detect at least one physiological parameter that has a threshold value or range indicative of an opioid overdose. Further, a controller can be mounted on the substrate and operatively coupled to the drug dispenser and the least one sensor. The controller can be configured to receive a signal detected by the least one sensor of the at least one physiological parameter to actuate release of the opioid antidote from the drug dispenser into the intestine of the patient upon a determination that the at least one physiological parameter falls outside a threshold value or range for the at least one physiological parameter indicating that an opioid overdose has been detected. For example, if the physiological parameter is respiratory rate, a threshold range can be approximately lower than 8 breaths per minute; if the physiological parameter is oxygen saturation, the threshold range can be below 85% to 90%.

In certain aspects, a sensor is an accelerometer that can detect motion of the abdomen during respiratory inhalation and exhalation as well as measuring other movement signals generated by the patient moving around (e.g. walking, coughing, or other physical activity). The sensor can be a 3-axis accelerometer, measuring linear acceleration in 3 dimensions. Inside the body, the accelerometer can pick up any full body movements (e.g. acceleration), but when the patient's body is at rest, one of the motions that is still present is movement of the gut during breathing (e.g. inhalation and exhalation cause movement of the abdomen and therefore movement of the rescue device). Hence suitable signal processing (e.g. filtering) can be applied to the accelerometer signals to isolate movement signal caused by respiration and thereby estimate respiratory rate. There are other types of motion in the GI tract like peristalsis that can be detected by the accelerometer, and certain cardiac ballistic activity (e.g. slight movements caused by blood flowing each beat of the heart) as well. During full body motion (e.g. walking) of the patient, the movement signals detected by the accelerometer may prevent accurate respiratory rate estimation, but for the sake of an overdose detection method, it can be assumed that if the patient is moving around and thus being physically active that the patient is not experiencing an overdose. Thus, the accelerometer sensing can be a two-step approach: if the patient is moving around, he or she is not overdosing. If the patient is at rest and the estimated respiratory rate drops below a threshold value or range, an overdose can be detected and an opioid antidote can be delivered and/or an alert sent to the patient or caregiver. The accelerometer signal processing can run in parallel with signals obtained by the PPG sensor as well, and a combination of estimates can provide more accurate estimates of respiratory rate along with SaO2.

As mentioned above, a non-refillable drug dispenser can be contained within the capsule of the opioid overdose rescue device and comprise an opioid antidote. The drug dispenser can contain any suitable opioid antidote including a plurality of opioid antidotes. The drug dispenser can be loaded in the capsule as the final manufacturing step and can include more than one drug dispenser, with each dispenser containing the same drug, different concentrations or release characteristics (e.g. extended, fast) of the same drug, or different drugs. Non-limiting examples of opioid antidotes including opioid antagonists such as naloxone, naltrexone, samidorphan, buprenorphine, or suitable combinations thereof. As stated above, naloxone is an opioid antagonist that can be injected in the muscle, vein or under the skin or sprayed into the nose. Due to first pass metabolism in the liver, the oral bioavailability of naloxone is only 2% making it impractical for direct delivery to the intestine, a problem which embodiments of the present disclosure address. In certain aspects, the opioid antidote is nalmefene. Nalmefene is a semisynthetic opiate receptor antagonist which is similar structurally to naltrexone and oxymorphone. Nalmefene is distinctive in having antagonist activity against all three types of opiate receptors—μ, κ and δ. When given intravenously or intramuscularly, nalmefene causes rapid onset of withdrawal symptoms in opioid dependent persons and has been used successfully to treat acute opioid overdose. It is also used to reverse opioid actions in the postoperative period. However, nalmefene has not often been delivered via an ingestible capsule to reverse the effects of an opioid overdose. It has a longer duration of action than naloxone and an oral bioavailability of 41% compared to 2% for naloxone. Injectable nalmefene was approved for use in the U.S. in 1995 as a therapy of opioid overdose. Similar to naloxone, in persons not taking opioids, nalmefene has minimal effects. Nalmefene is extensively metabolized in the liver, but largely by glucuronidation rather than transformation to a different metabolite. Patients with opioid overdose often have underlying chronic liver diseases such as alcoholic liver disease, hepatitis B or C, but treatment with nalmefene does not appear to exacerbate those conditions.

While many schedules of opiate receptor antagonist release are possible, an example would be an initial automatic release by the device of 0.5 mg of nalmefene followed by monitoring for 90 seconds. If physiological parameters are unchanged or worsen, an additional 0.5 mg of nalmefene could be automatically released followed by an additional monitoring period of 90 seconds. That cycle could continue until a total of 20 mg of nalmefene had been released or physiological parameters improved. Throughout the delivery of therapy, the device could store samples of physiological signals in its memory and datalog the time of drug release and data storage. The stored information could be uploaded automatically along with alerts to the patient's cell phone for subsequent uploading to a centralized database for review by authorized clinicians.

In another embodiment of this invention, the device can be configured to deliver nalmefene directly in the intestines based on a programmed schedule. For instance, at set intervals spanning hours or days the ingestible device could release small doses of nalmefene to prolong the pharmacological effect of the opioid antagonist. Intervals and doses can be programmed by a clinician customized to the needs of the patient. In this embodiment, the device may also deliver an initial larger opioid overdose rescue dose (e.g. 5+ mg) if detected by the physiological sensors, and then subsequently continue release of smaller doses of nalmefene over an extended period of time (many hours or days) to protect the individual from subsequent overdose events. The dosage for these prolonged administrations can be titrated to have the desired preventative effect but not cause undesirable opioid withdrawal symptoms. Upon depletion of the nalmefene, a wireless command can be sent to the smartphone to inform the user and/or clinician that a new ingested device would be required to continue delivery of nalmefene if clinically desired.

EXAMPLES

The following examples provides data collected from an opioid overdose rescue device during overdose and rescue animal studies. The opioid overdose rescue device included a substrate having a PPG sensor, accelerometer and microcontroller disposed thereon, which was coupled to a substrate having a radio, chip antenna, power management components, and magnet sensor (so the device could be turned on and off without direct contact) disposed thereon.

Figure 6A:
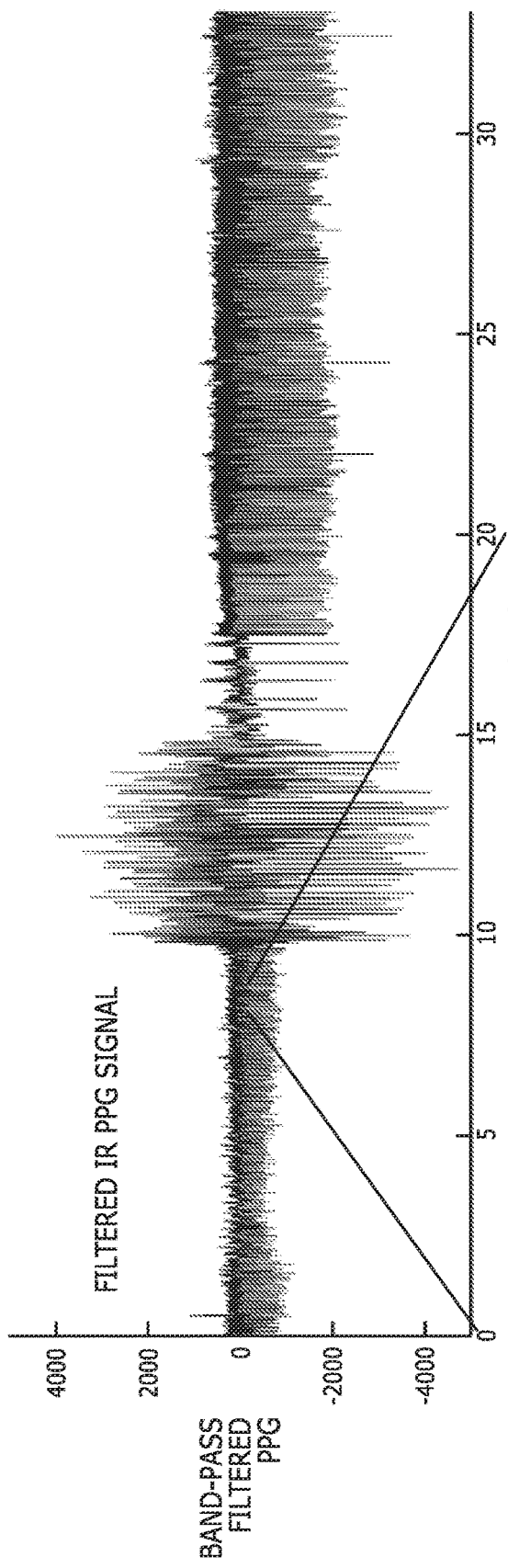
FIGS. 6A and 6B are photoplethysmograms obtained during an induced morphine overdose of pigs as described below which demonstrate that cardiac and respiratory signals be extracted from PPG sensor data.
Figure 6B:
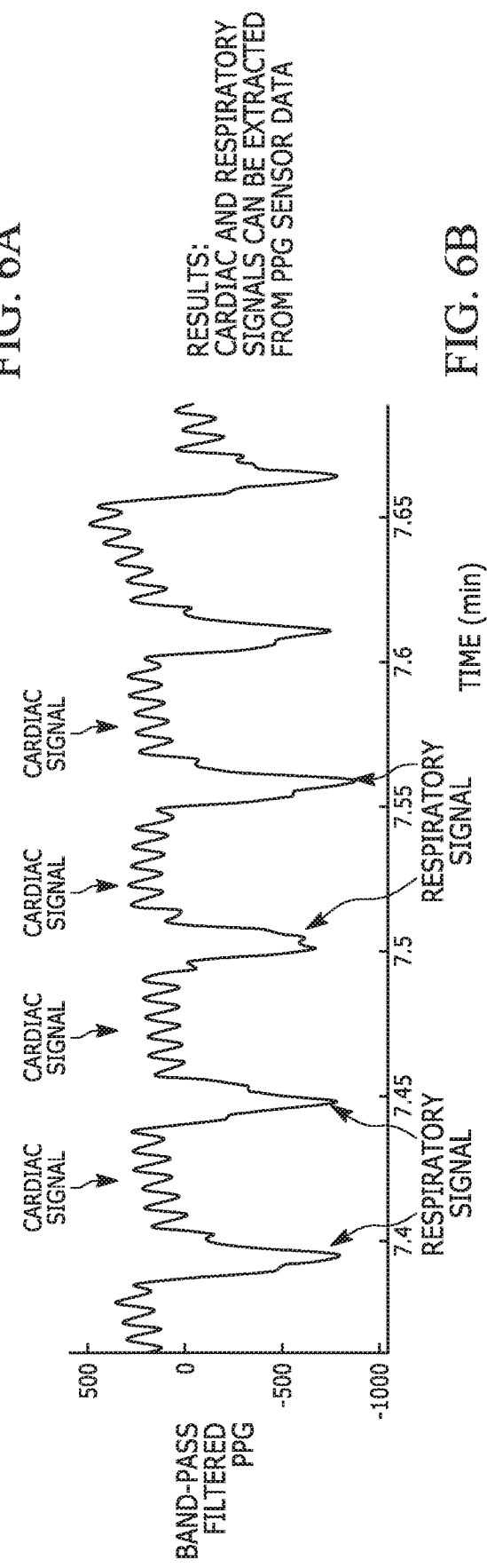

FIGS. 6A and 6B show an example PPG sensor recording from the intestines in an anesthetized porcine animal model during an overdose and recovery study. The PPG sensor was endoscopically placed into the small intestine and anchored to intestinal tissue with 2 endoclips—one on each side of the device. FIG. 6A shows a 33 minute trace of PPG signal that has been band-pass filtered from 0.1 to 5 Hz. FIG. 6B shows a zoomed in view of approximately 30 seconds of IR PPG data to highlight the smaller amplitude, higher frequency cardiac waveforms and also the larger amplitude, less frequent respiratory waveforms that are both captured in the signal.

Figure 7A:
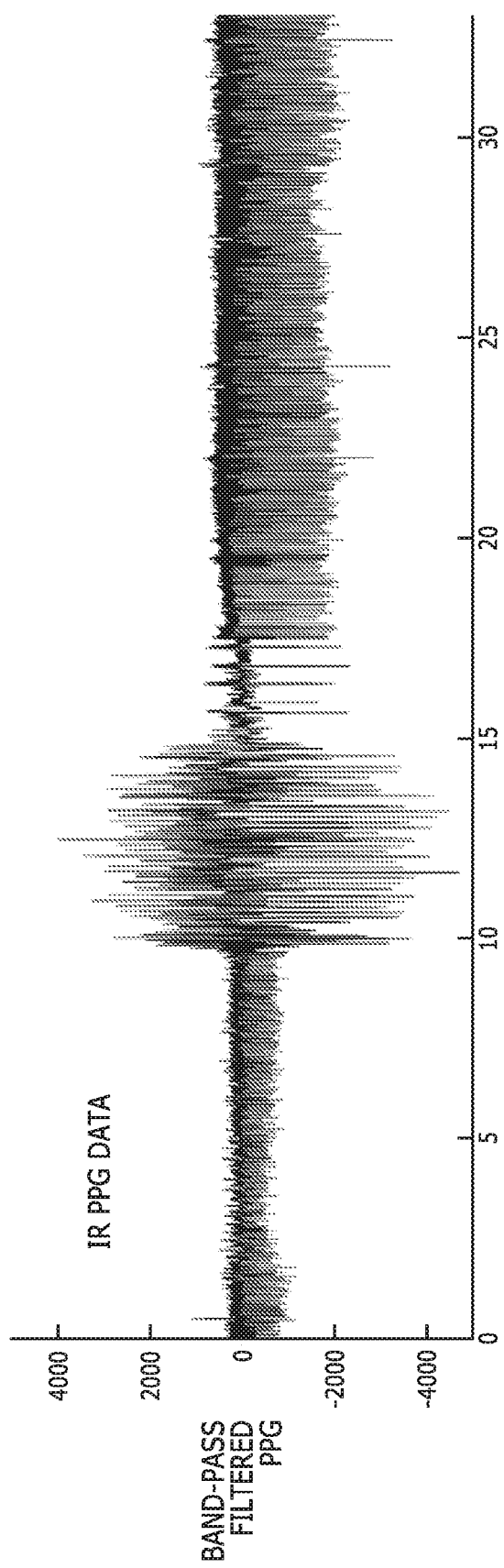
FIG. 7A is a photoplethysmogram obtained during an induced morphine overdose of pigs and mitigation of such overdose with nalmefene as described below.
Figure 7B:
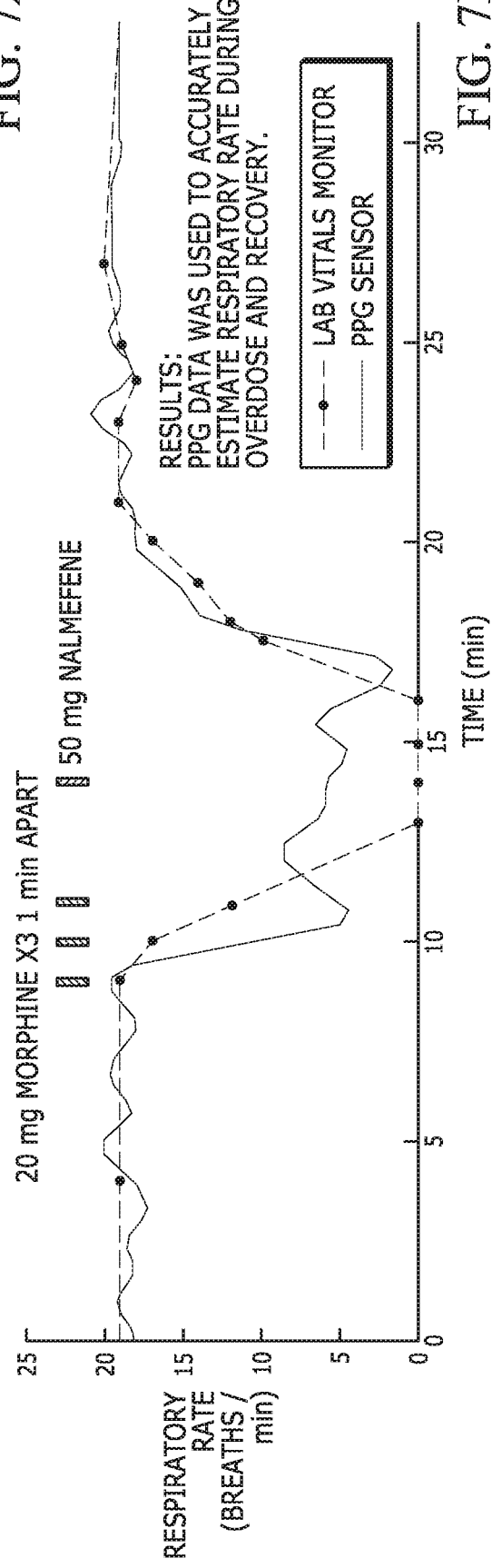
FIG. 7B is graph of the estimated respiratory rate extracted from the photoplethysmogram of FIG. 7A demonstrating that PPG sensor data can be used to accurately estimate respiratory rate during overdose and recovery.

FIGS. 7A and 7B demonstrate using the PPG signal to estimate respiratory rate during overdose and recovery. Baseline data was collected for 8 minutes. Then 60 mg of IV morphine was administered over 3 minutes (20 mg each minute for 3 minutes). The respiratory rate as measured by the lab vitals monitoring equipment decreased eventually to zero, indicated respiratory failure. One minute after respiratory failure, 50 mg nalmefene in solution was administered endoscopically directly into the intestines. Within 4 minutes of nalmefene delivery breathing recovered and eventually returned to pre-overdose levels. Using the respiratory waveforms observed in the PPG signals described in FIG. 6B, an offline analysis was performed to estimate the animal's respiratory rate during the study and is shown in FIG. 7B overlaid with the lab vitals monitor respiratory rate. The respiratory rate measurements from the PPG sensor match well with the values from the vitals monitor. In certain aspects, a method of mitigating the effects of an opioid overdose could involve determining when a measured respiratory rate drops below a threshold (e.g. 8 breaths per minute) for a duration of time (e.g. 30 seconds) and commanding release of a rescue medication.

Figure 8A:
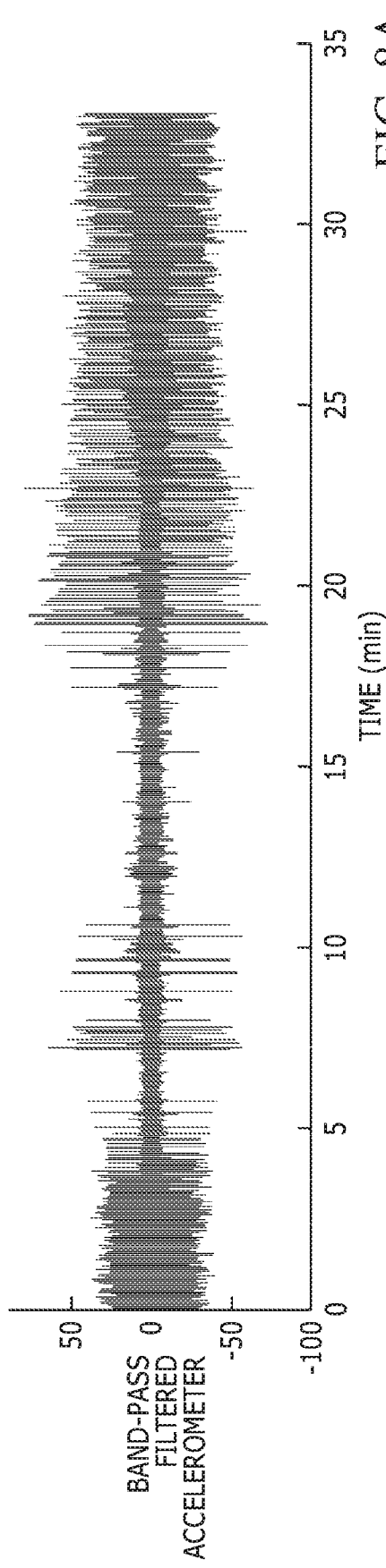
FIG. 8A is a graph of wireless accelerometer data obtained during an induced morphine overdose of pigs and mitigation of such overdose with nalmefene as described below.
Figure 8B:
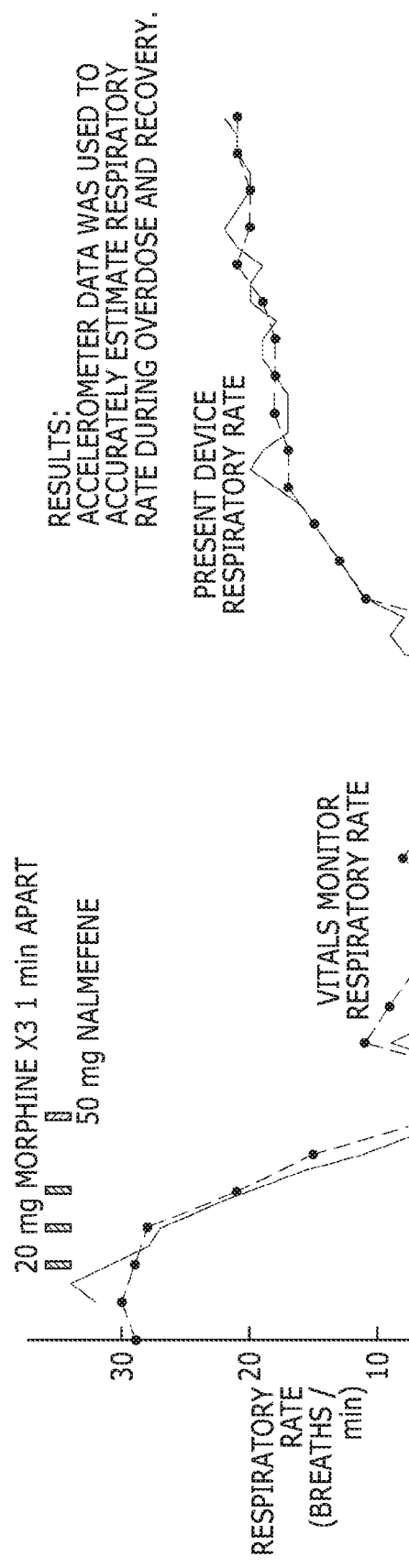
FIG. 8B is graph of the estimated respiratory rate extracted from the accelerometer data of FIG. 8A demonstrating that accelerometer sensor data can be used to accurately estimate respiratory rate during overdose and recovery.

FIGS. 8A and 8B demonstrate using an accelerometer sensor to measure respiratory rate during overdose and recovery. In a different study than referenced in FIG. 7, the device was endoscopically placed and anchored in the animal's intestine in a similar manner. In this study the same amount of morphine was delivered—60 mg IV morphine over 3 minutes. Respiratory rate similarly decreased to zero indicating respiratory failure. 50 mg nalmefene in solution was also endoscopically delivered. 14 minutes after nalmefene delivery respiratory rate was restored to normal levels. FIG. 8A shows band-pass filtered accelerometer signals (x axis of the 3-axis sensor) throughout the overdose and recovery. Each 'spike' observed in the data represents a single breath or respiratory waveform. Similar to the study described in FIG. 7 with the PPG sensor, respiratory rate was estimated using the accelerometer signal and as shown in FIG. 8B, the respiratory rate derived from the accelerometer matched well with the lab vitals monitor. As with the PPG data, a measured respiratory rate obtained from the motion sensing (i.e. accelerometer) data in the intestine could be used to detect an opioid overdose and trigger delivery of a rescue medication.

Each of the disclosed aspects and embodiments of the present disclosure may be considered individually or in combination with other aspects, embodiments, and variations of the disclosure. Further, while certain features of embodiments and aspects of the present disclosure may be shown in only certain figures or otherwise described in the certain parts of the disclosure, such features can be incorporated into other embodiments and aspects shown in other figures or other parts of the disclosure. Along the same lines, certain features of embodiments and aspects of the present disclosure that are shown in certain figures or otherwise described in certain parts of the disclosure can be optional or deleted from such embodiments and aspects. Additionally, when describing a range, all points within that range are included in this disclosure. Further, unless otherwise specified, none of the steps of the methods of the present disclosure are confined to any particular order of performance. Furthermore, all references cited herein are incorporated by reference in their entirety.

What is claimed is:
1. An opioid overdose rescue device to mitigate the effects of an opioid overdose in a patient who has taken an opioid comprising:
    an ingestible capsule;
    a non-refillable drug dispenser contained within the capsule and comprising an opioid antidote;
    an accelerometer contained within the capsule configured to sense movement signals within the patient's gastrointestinal tract caused by peristalsis and respiration and generate accelerometer signals; and
    a controller operatively coupled to the drug dispenser and the accelerometer, the controller configured to receive the accelerometer signals and produce processed accelerometer signals from the gastrointestinal tract that isolate movement signals caused by respiration to estimate a respiratory rate of the patient and to actuate drug release of the opioid antidote from the drug dispenser into the patient upon a determination that the respiratory rate falls outside a threshold value or range indicating that an opioid overdose has been detected.

2. The device of claim 1, further comprising a substrate contained within the capsule, the controller mounted on the substrate, the substrate having a furled configuration within the capsule and an unfurled configuration when ingested and released from the capsule into the patient.

3. The device of claim 1, wherein the capsule comprises an enteric coating.

4. The device of claim 1, wherein the opioid antidote is nalmefene.

5. The device of claim 1, further comprising an anchor connected to a substrate contained within the capsule and sized and configured to attach to the mucosal surface of the patient's intestine.

6. The device of claim 1, further comprising a power controller electrically connected to the controller.

7. The method of claim 1, wherein the processed accelerometer signals comprise band-pass filtered accelerometer signals.

8. The device of claim 1, further comprising a radio configured to communicate with an external device, wherein the controller is configured to control the operation of the radio to send an alert to the external device in response to determining that the subject is undergoing an opioid overdose.

9. The device of claim 8, wherein the radio comprises a wireless radio, and the external device comprises a smartphone.

10. The device of claim 1, further comprising a clock and a memory module both of which are operatively connected to the controller, wherein the controller is configured to timestamp data with time information from the clock and store the timestamped data in the memory module.

11. The device of claim 10, wherein the timestamped data comprises respiration data of the patient, cardiac activity of the patient, overdose data of the subject, or combinations thereof.

12. The device of claim 1, further comprising at least one other sensor contained with the capsule and configured to detect at least one physiological parameter that has a threshold value or range indicative of an opioid overdose.

13. The device of claim 12, wherein the controller is operatively coupled the least one other sensor, the controller configured to receive a signal detected by the least one other sensor of the at least one physiological parameter to actuate release of the opioid antidote from the drug dispenser into the patient upon a determination that the at least one physiological parameter falls outside a threshold value or range for the at least one physiological parameter indicating that an opioid overdose has been detected.

14. The device of claim 12, wherein the at least one other sensor is a photoplethysograph (PPG) sensor, an impedance plethysmograph (IPG) sensor, an electrocardiogram (ECG) sensor, a temperature sensor, or combinations thereof.

15. The device of claim 12, further comprising a power supply configured to provide electrical power for operating the controller, the at least one other sensor, and the drug dispenser.

16. The device of claim 12, wherein the controller, the accelerometer, and the at least one other sensor are formed at least partially as an application specific integrated circuit (ASIC).

17. The device of claim 12, wherein the at least one physiological parameter is heart rate, heart rate variability, blood oxygen saturation, core temperature, blood pressure, or combinations thereof.

18. The device of claim 12, wherein the at least one physiological parameter is intestinal wall color.

\* \* \* \* \*